US00PP19469P2

(12) United States Plant Patent
Rinck

(10) Patent No.: US PP19,469 P2
(45) Date of Patent: Nov. 18, 2008

(54) SCENTED GERANIUM PLANT NAMED 'FROSTED'

(50) Latin Name: *Pelargonium citrosum*
Varietal Denomination: Frosted

(76) Inventor: Michael C. Rinck, Agristarts III, Inc., 19825 SR 44, Eustis, FL (US) 32736

( * ) Notice: Subject to any disclaimer, the term of this patent is extended or adjusted under 35 U.S.C. 154(b) by 0 days.

(21) Appl. No.: 11/881,421

(22) Filed: Jul. 27, 2007

(51) Int. Cl.
*A01H 5/00* (2006.01)

(52) U.S. Cl. ..... Plt./324
(58) Field of Classification Search ..... Plt./324
See application file for complete search history.

(56) References Cited

PUBLICATIONS

Logee's Tropical Plants for 'Frosted' (G4086–2), Logee's Greenhouse LTD 2008 [online] [retrieved on May 1, 2008], retrieved from the Internet at <http://www.logees.com/prod-info.aspnumber?=G4086–2> 2 pages.*

* cited by examiner

*Primary Examiner*—Kent L. Bell
*Assistant Examiner*—June Hwu
(74) *Attorney, Agent, or Firm*—Penny J. Aguirre

(57) ABSTRACT

A new cultivar of Scented geranium, *Pelargonium citrosum* 'Frosted', characterized by its citronella-scented dark green leaves with deeply incised lobes tips or "frosted" in white, its pink tinged newly emerging foliage, its compact plant habit with numerous basal branches and short leaf internodes, its heat tolerance, and its vigor and ease of propagation by tissue culture.

3 Drawing Sheets

Botanical classification: *Pelargonium citrosum.*
Cultivar designation: 'Frosted'.

BACKGROUND OF THE INVENTION

The present invention relates to a new and distinct cultivar of Scented Geranium plant, botanically known as *Pelargonium citrosum* 'Frosted' and will be referred to hereafter by its cultivar name, 'Frosted'. The new cultivar is an ornamental plant and suitable for use as a container or bedding plant.

The inventor discovered the new cultivar, 'Frosted', in the greenhouse of a tissue culture laboratory in Apopka, Fla. in April of 2006. 'Frosted' arose as a naturally occurring branch mutation of *Pelargonium citrosum* 'Van Leenii' during in vitro propagation.

Asexual reproduction of the new cultivar was first accomplished by in vitro propagation under direction of the inventor in Apopka, Fla. in April 2006. Propagation by tissue culture has determined that the characteristics of this cultivar are stable and are reproduced true to type in successive generations.

SUMMARY OF THE INVENTION

The following traits have been repeatedly observed and represent the characteristics of 'Frosted'. These attributes in combination distinguish 'Frosted' as a new and distinct cultivar of Scented geranium.

1. 'Frosted' exhibits leaves that are dark green with white variegation on the tips of the leaf lobes.
2. The plant habit of 'Frosted' is compact; exhibiting numerous basal branches and branches with short internodes between leaves.
3. The new leaves of 'Frosted' exhibit a tinge of pink coloration on its leaf tips when grown in full sun.

4. 'Frosted' may bloom during spring and summer with corymbs of light lavender to white flowers with deep purple markings.
5. The foliage of 'Frosted' is citronella-scented.
6. 'Frosted' is tolerant to summer heat and has been grown in temperatures of 90 to 95° F. without leaf tip burning.

The new cultivar, 'Frosted', differs from its parent plant, 'Van Leenii', in having variegated foliage, a more compact plant habit, emerging foliage with pink tinged leaf tips, and a better tolerance for heat with less foliage burn when grown in high temperatures. There are other cultivars variegated scented geraniums known to the inventor; none of which have citronella-scented foliage. The closest comparison cultivar in terms of leaf characteristics is *Pelargonium graveolens* 'Variegata', commonly known as Variegated rose geranium (not patented) and differs from 'Frosted' in having rose scented foliage, silver tipped leaves rather than white, and by blooming with lavender colored flowers.

BRIEF DESCRIPTION OF THE DRAWING

The accompanying colored photographs illustrate the overall appearance and distinct characteristics of the new Scented geranium. The photographs depict plant and plant parts of a plant 3 months in age as grown in a 6 cm container under greenhouse conditions in Apopka, Fla.

The photograph in FIG. 1 is a side view of a plant of 'Frosted'.

Figure 1:
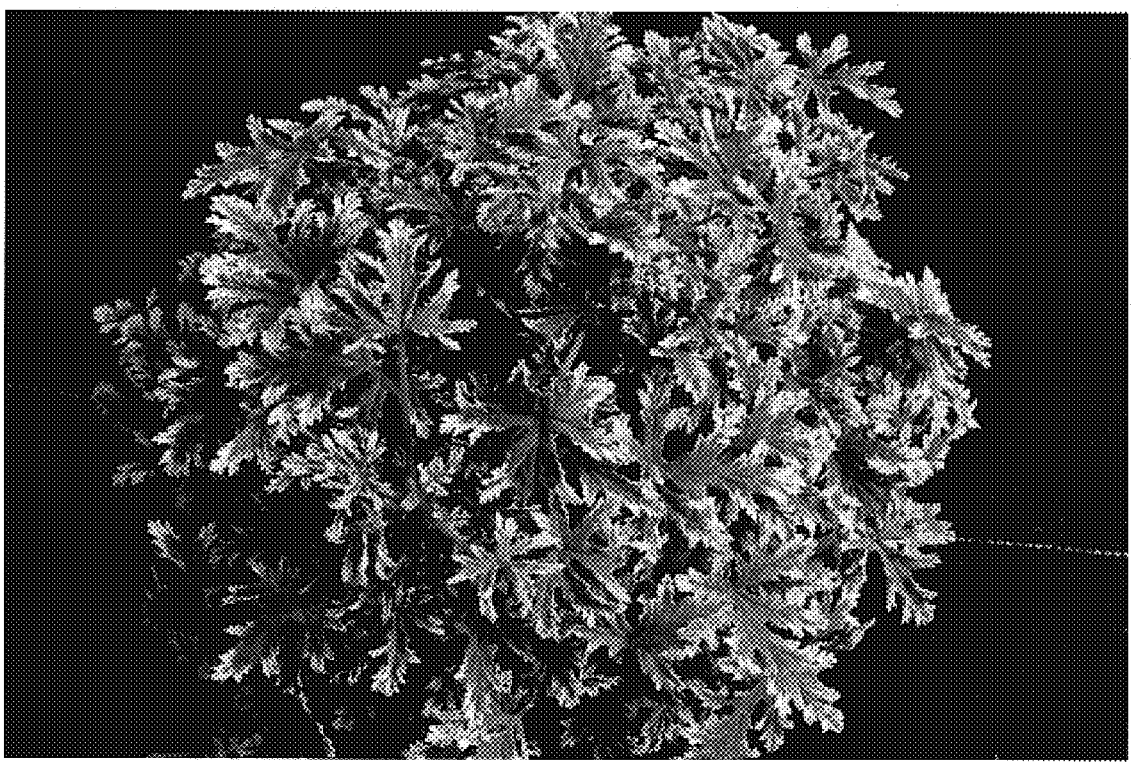
Figure 2:
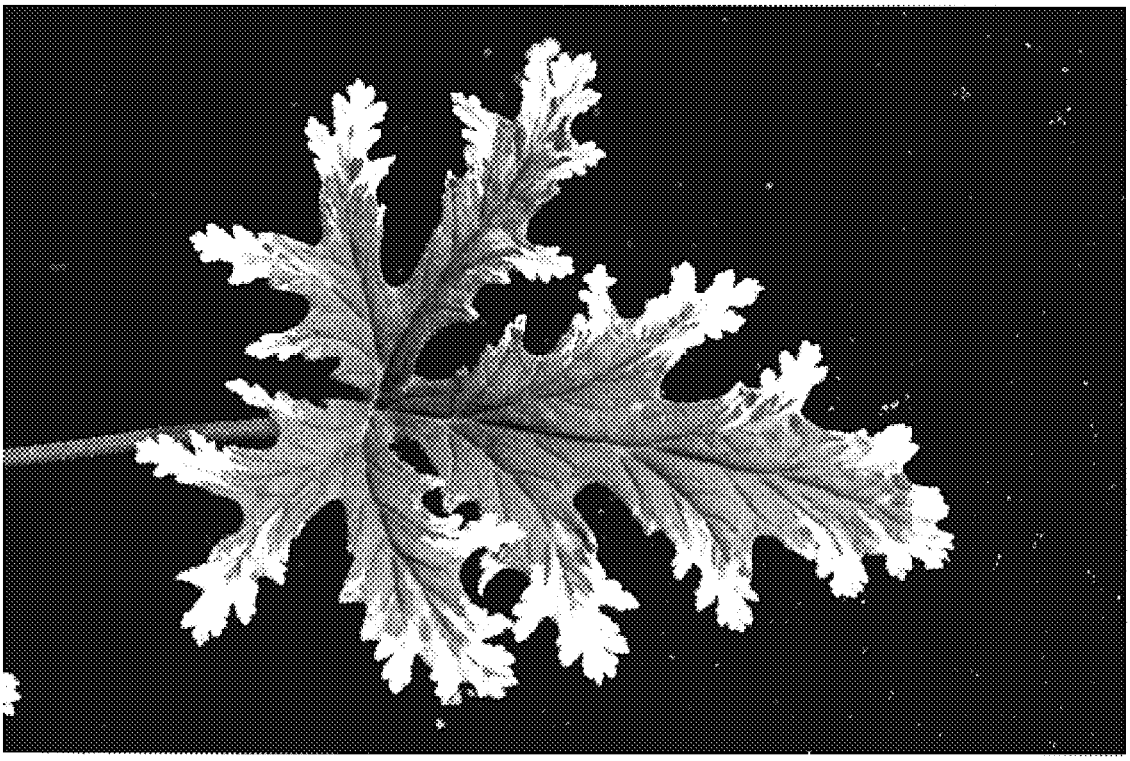
Figure 3:
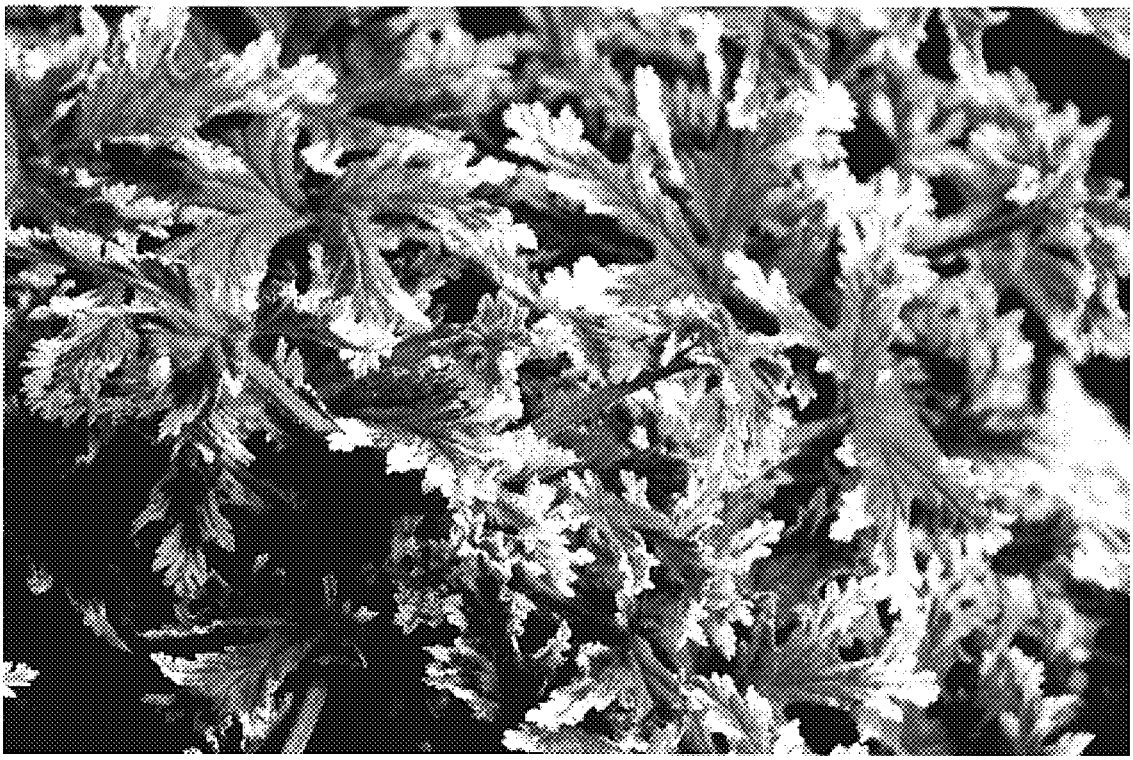

The photograph in FIG. 2 is of a close-up view of a mature leaf of 'Frosted' while the photograph in FIG. 3 provides a close-up view of the newly emerging foliage of 'Frosted'.

Figure 4:
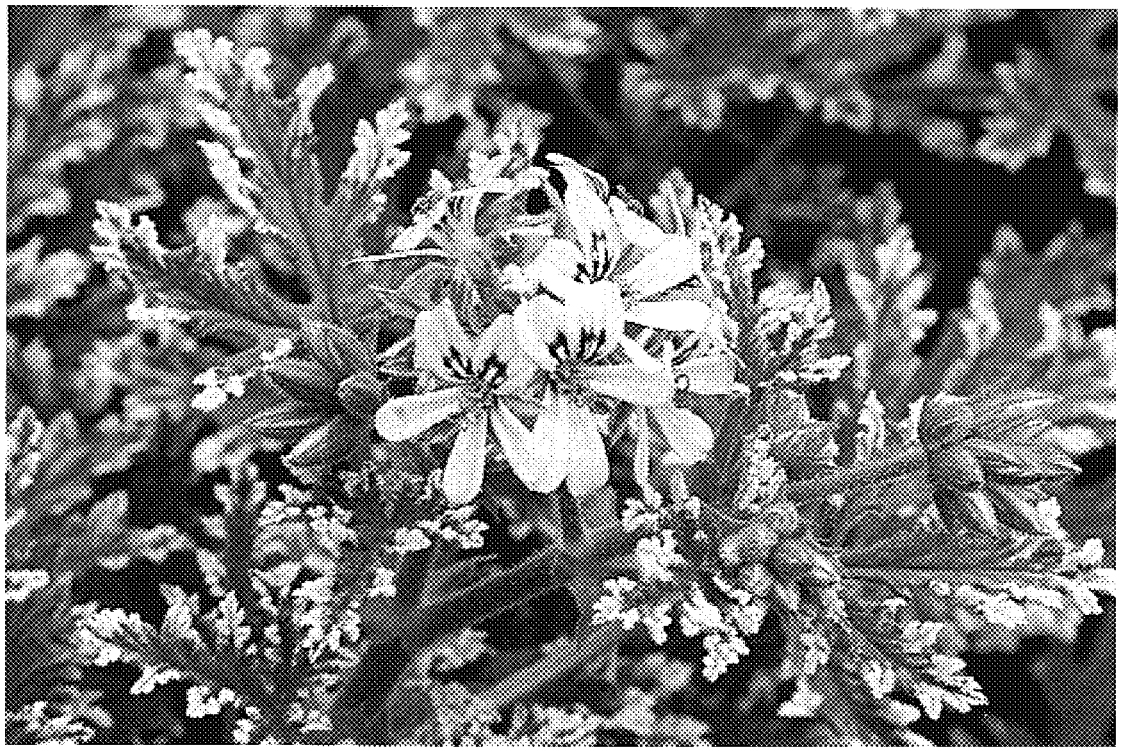

The photograph in FIG. 4 provides a close-up view of the flowers of 'Frosted'.

The colors in the photographs are as close as possible with the photographic and printing technology utilized. The color values cited in the detailed botanical description accurately describe the colors of the new Scented geranium.

DETAILED BOTANICAL DESCRIPTION OF THE PLANT

The following is a detailed description of 3 month-old plants of new cultivar as grown in a 6 cm container under greenhouse conditions in Apopka, Fla. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Frosted' is a cultivar of *Pelargonium citrosum.*

Parentage: Branch mutation of *Pelargonium citrosum* 'Van Leenii'.

General characteristics:

*Bloom.*—'Frosted' may bloom under the right conditions from spring through summer.

*Plant habit.*—Compact, mound of dense foliage.

*Height and spread.*—Reaches about 30 cm in height and 30 to 35 cm in spread.

*Cold hardiness.*—At least to U.S.D.A. Zone 10.

*Heat tolerance.*—At least tolerant to temperature up to 95° F. without observation of burning of the leaf tips.

*Diseases and pests.*—No susceptibility or resistance to diseases or pests has been observed.

*Root description.*—Fine and dense.

Growth and propagation:

*Growth rate.*—Vigorous until rooted in a 6 cm container, then moderate.

*Propagation.*—In vitro propagation.

*Time required for root initiation.*—About 10 days in Stage 3 media under tissue culture lab conditions.

*Time required for root development.*—About 2 weeks from a stage 3 plantlet to develop a 1 inch liner, a 6 cm container planted with a 1 inch liner will fully develop within 6 weeks.

Stem description:

*Stem size.*—Average of 17 cm in length and 7 mm in width.

*Stem strength and aspect.*—Stout, strong, held upright to a 45° angle.

*Stem shape.*—Slightly oval.

*Stem color.*—144A to 144B.

*Stem surface.*—Pubescent.

*Branching habit.*—Numerous basal branches, a 6 cm container planted with a 1 inch plug produces an average of 7 branches.

Foliage description:

*Leaf shape.*—Ovate in outline.

*Leaf division.*—Simple.

*Leaf base.*—Hastate.

*Leaf apex.*—Acute.

*Leaf venation.*—Palmate, conspicuously recessed on upper surface, color between 147A and 146A on upper surface and 145D in color on lower surface, puberulent on both surfaces.

*Leaf margins.*—Palmately parted, lobes incised with 1 terminal lobe, 2 lateral lobes, and 2 basal lobes.

*Leaf attachment.*—Petiolate.

*Leaf arrangement.*—Alternate to whorled.

*Leaf variegation pattern.*—Green centers and with lobe incisions white or white with green markings as coded below, small amount of grey-green intermediate area exists in irregular pattern between lobe tips and centers; 189A in color.

*Leaf internode length.*—Ranges from tightly congested to 1.2 cm, average of 5 mm.

*Leaf surface.*—Upper surface is dull and puberulent.

*Leaf color.*—Young upper surface; 146B with leaf tips 155A tinged with 36D if grown in full sun, young lower surface; 147A with leaf tips 155A tinged with 36D when grown in full sun, mature upper surface; color between 147A and 146A with leaf tips 155A, mature lower surface; 147B with leaf tips 155A.

*Leaf size.*—Average of 8.5 cm in length and 7.5 cm in width when mature, terminal lobe averages 5 cm in length and 4 cm in width, lateral lobes average 3 cm in length and 1.5 cm in width, basal lobes average 2.5 cm in length and 1.5 cm in width.

*Leaf quantity.*—Average of 12 per lateral branch 12 cm in length with new leaves forming at nodes for future development.

*Petioles.*—Average of 11 cm in length and 2 mm in width on mature leaves, 146B in color, surface is pubescent.

*Stipules.*—Two per petiole, lanceolate in shape, acute apex, broadly truncate base, average of 7 mm in length and 8 mm in width, 146B in color and puberulent on both surfaces.

Flower description:

*Inflorescence type.*—Corymb of single, rotate flowers at terminals of lateral branches.

*Inflroescence size.*—Average of 6 cm in diameter and 5 cm in depth.

*Lastingness of flowers.*—About 7 days on the plant, sepals persistent.

*Flower size.*—Average of 8 mm in height and 1.6 cm in diameter.

*Flower fragrance.*—None.

*Flower number.*—Average of 7 per inflorescence.

*Flower aspect.*—Outward.

*Flower buds.*—Elliptic in shape, average of 1.3 cm in length and up to 6 mm in width, 138B in color with areas of N155B, surface is pubescent.

*Corolla features.*—Petals are unfused and arranged in a rotate form, slightly reflexed.

*Petal number.*—5.

*Petal shape.*—Oblanceolate.

*Petal color.*—Opening upper and lower surface; whiter than N155B with center markings of 61A, fully open upper and lower surface; whiter than N155B with center markings of 61A and lightly suffused with 84C to 84D.

*Petal surface.*—Glabrous.

*Petal margins.*—Entire.

*Petal apex.*—Rounded with a single notch on some petals.

*Petal size.*—Average of 8 mm in length and 4 mm in width.

*Calyx form.*—Rotate with sepals held nearly horizontal.

*Sepals.*—5, elliptic in shape, average of 8 mm length and 4 mm in width, entire margin, acute apex, cuneate base, pubescent on both surfaces, color when young and mature upper and lower surface 138B in color with vertical stripes of N155B (slightly whiter).

*Peduncles.*—Slightly oval in shape, average of 2.6 cm in length and 2 mm in diameter, strong, held at about a 90° angle relative to lateral branch, color a blend of 144A and N137D, surface is pubescent.

*Pedicels.*—Slightly oval in shape, average of 5 mm in length and 1.5 mm in width, strong, held at about a 45° angle relative to peduncle, color a blend of 144A and N137D, surface is pubescent.

Reproductive organs:

*Gynoecium.*—1 pistil, about 8 mm in length, 5 stigmas are decurrent and 76A in color, style is about 6 mm in length and 76B in color, ovary is 144B to 144C in color.

*Androcoecium.*—5 stamens, anthers are dorsifixed, oblong in shape, 2 mm in length, and 162D in color, filaments are 6 mm in length and 162D in color, pollen was not discernable.

*Fruit/seeds.* —Fruit and seed production was not observed.

I claim:

1. A new and distinct cultivar of Scented geranium plant named 'Frosted' as herein illustrated and described.

* * * * *